United States Patent [19] [11] Patent Number: 6,142,946
Hwang et al. [45] Date of Patent: Nov. 7, 2000

[54] ULTRASONIC DIAGNOSTIC IMAGING SYSTEM WITH CORDLESS SCANHEADS

[75] Inventors: Juin-Jet Hwang, Mercer Island; Lauren S. Pflugrath, Seattle; Leo R. Catallo, Mercer Island, all of Wash.

[73] Assignee: ATL Ultrasound, Inc., Bothell, Wash.

[21] Appl. No.: 09/197,398

[22] Filed: Nov. 20, 1998

[51] Int. Cl.[7] ........................................ A61B 8/14
[52] U.S. Cl. ............................................... 600/459
[58] Field of Search .......................... 600/437, 443–447, 600/453, 459; 73/625–627; 364/708.1, 725, 606, 844; 382/128, 132

[56] References Cited

U.S. PATENT DOCUMENTS

| | | |
|---|---|---|
| 4,413,629 | 11/1983 | Durley, III . |
| 5,295,485 | 3/1994 | Shinomura et al. . |
| 5,590,658 | 1/1997 | Chiang et al. . |
| 5,640,960 | 6/1997 | Jones et al. . |
| 5,690,114 | 11/1997 | Chiang et al. . |
| 5,715,823 | 2/1998 | Wood et al. . |
| 5,722,412 | 3/1998 | Pflugrath et al. . |
| 5,851,186 | 12/1998 | Wood et al. ............................. 600/437 |
| 5,865,733 | 2/1999 | Malinouskas et al. . |
| 5,882,300 | 3/1999 | Malinouskas et al. . |
| 5,964,709 | 10/1999 | Chiang et al. ........................... 600/447 |

FOREIGN PATENT DOCUMENTS

| | | |
|---|---|---|
| 0 762 142 | 3/1997 | European Pat. Off. . |
| 0 833 266 | 4/1998 | European Pat. Off. . |
| 55-151952 | 11/1980 | Japan . |
| WO 96/32888 | 10/1996 | WIPO . |

OTHER PUBLICATIONS

Emery et al., "Optoelectronic Transmitters for Medical Ultrasound Transducers," IEEE, 1994 Ultrasound Symposium, Duke University, Durham, NC, pp. 1519–1522.

*Primary Examiner*—Marvin M. Lateef
*Assistant Examiner*—Ali M. Imam
*Attorney, Agent, or Firm*—W. Brinton Yorks, Jr.

[57] ABSTRACT

An ultrasonic diagnostic imaging system is provided with cordless scanheads which wirelessly transmit ultrasonic image signals to the imaging system. The transmitted image signals are received by a receiver in the mainframe ultrasound system where they undergo further image processing and are displayed. In a preferred embodiment the scanhead image signals are at least partially beamformed in the scanhead before being transmitted to the ultrasound system, thereby reducing the required transmission bandwidth. The cordless scanheads are battery powered, and are recharged by the ultrasound system when the scanheads are not being used for scanning.

77 Claims, 11 Drawing Sheets

ULTRASONIC DIAGNOSTIC IMAGING SYSTEM WITH CORDLESS SCANHEADS

This invention relates to ultrasonic diagnostic imaging systems and, in particular, to ultrasonic diagnostic imaging systems in which the scanning of patients is done by cordless scanheads.

Ultrasonic diagnostic imaging systems have traditionally been thought of as having two major constituent parts: a probe or scanhead, and the mainframe processor or system. The probe contains the piezoelectric transmitter and receiver of ultrasonic energy which is used to scan the patient's body. The system contains the sophisticated electronic controllers and processors which control the probe and turn the received echo signals into diagnostic images and information. But there is one additional ever-present component: the cable which connects the probe to the system, through which power and signals are coupled between the probe and system.

The probe cable has taken many forms as it has evolved over the years, and has had varying impacts on physician and patient comfort and convenience. Early products which only were used for audio Doppler or A-line (single line) imaging needed very few wires in the cable. Since the probes for such products generally used single element or single piston transducers, sometimes referred to as "pencil probes," signal and ground wires often sufficed as a complete cable. Such a probe had an unsteered, fixed focus along a single beam. The user adjusted the probe by physically moving it to a different position or offsetting it from the body with an acoustic standoff. While the thin, light cable was convenient to lift and maneuver, the caliber of the diagnostic information obtained was minimal.

The advent of B arm systems took convenience in a different direction. In these systems the probe was attached to the end of an articulated arm which provided probe position information for two dimensional imaging. The step-up in diagnostic image quality was at the expense of the articulated arm, which constrained imaging to its range of movement. Merged into the articulated arm, the cable was virtually unnoticeable in the ungainly mechanism.

Greater freedom of movement returned with the development of the mechanical sector scanner probe. The mechanical sector scanner oscillated the transducer back and forth to scan the image field, and the oscillating mechanism provided the spatial orientation for two dimensional imaging. A single piston transducer with two wires, signal and ground, was needed, as well as wires to power and control the oscillating mechanism and send the spatial orientation signals to the system. The hand-held probe was convenient, but the cable was beginning to grow in size.

Cable growth accelerated considerably with the advent of solid-state or array probes. In the array probes the transducer comprises an array of dozens or hundreds of elements which are individually controlled to electronically steer and focus the ultrasound beam. But with individual control comes the need for individual wires: a 128 element transducer probe can require a cable with 128 individual wires. Since received echo signals are generally of very low levels, the wires are not simply stranded wires, but coaxial lines, each with its own signal line and conductive shield. While various multiplexing schemes in the probe have been used to reduce the number of wires in the cable, these schemes can have adverse consequences for performance criteria such as frame rate, aperture size, and control complexity. Accordingly it would be desirable to reduce the size of the probe cable, or even eliminate it, thereby improving clinician and patient convenience but without incurring any performance penalties.

In accordance with the principles of the present invention, an ultrasonic diagnostic imaging system is presented in which the probe cable is eliminated, giving rise to the utmost convenience for the clinician and patient. This convenience is brought about by the inclusion of a wireless transmitter in the probe case, eliminating the need to connect the probe to the mainframe ultrasound system. The ultrasound system includes a receiver for receiving the ultrasound information from the probe. In a preferred embodiment the transmission bandwidth is kept low by doing at least some beamforming in the probe itself, so that only beamformed echoes need be transmitted to the mainframe system, replacing the 128 wires from the individual transducer elements of the array probe mentioned above. The complete elimination of the probe cable provides the ultimate in ultrasonic scanning ease and convenience.

Figure 1:
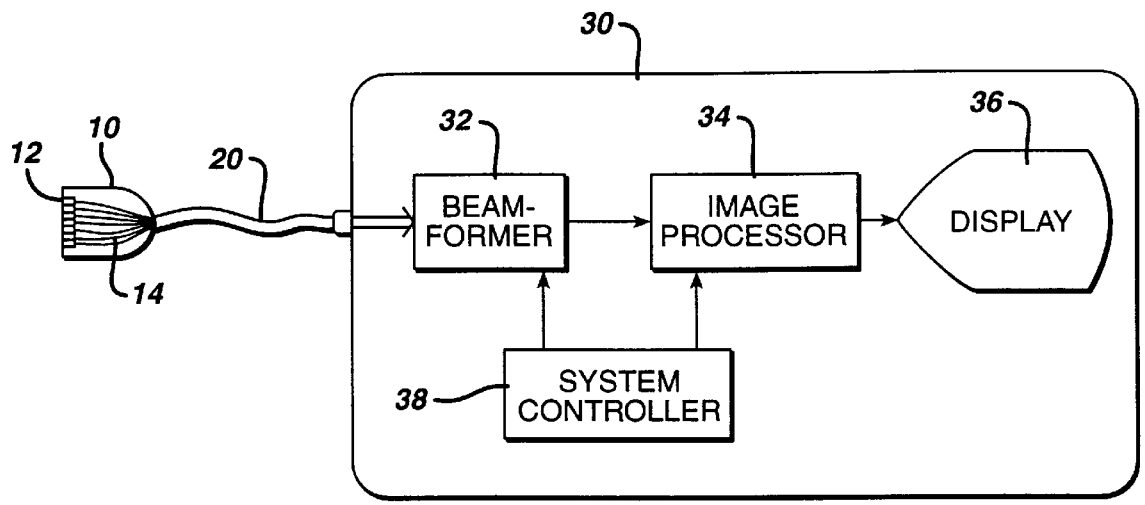
FIG. 1 illustrates in block diagram form the conventional configuration of an ultrasonic probe, cable, and ultrasonic imaging system.

Referring first to FIG. 1, a conventional ultrasonic probe, cable and imaging system arrangement is shown in block diagram form. The ultrasonic probe 10 includes a transducer array 12. Conductors 14 connect individual elements of the transducer array to conductors inside a cable 20, which connects to an ultrasonic imaging system 30. The conductors of the cable are electrically connected to a beamformer 32 in the imaging system, which controls the timing of the pulsing of the elements of the transducer array, and delays and sums received echo signals from the transducer elements to form coherent beams of echo signals. The beamformed echo signals are coupled to an image processor 34 where they are processed to form an image of tissue or flow within the body of the patient being scanned. The resultant ultrasonic image is displayed on an image display 36. Coordination of the processing and data flow of the beamformer 32 and image processor 34 is provided by a system controller 38, which receives instructions from a user by way of various user controls.

While the elements of the transducer array 12 are shown directly wired to the conductors of the cable in FIG. 1, multiplexers can be included within the probe between the array elements and the cable to reduce the number of cable conductors. It is then necessary to control the multiplexers from the ultrasound system with control lines, so that the cable conductors are multiplexed to the elements of the current active aperture each time the probe is transmitting or receiving ultrasonic signals.

Figure 2:
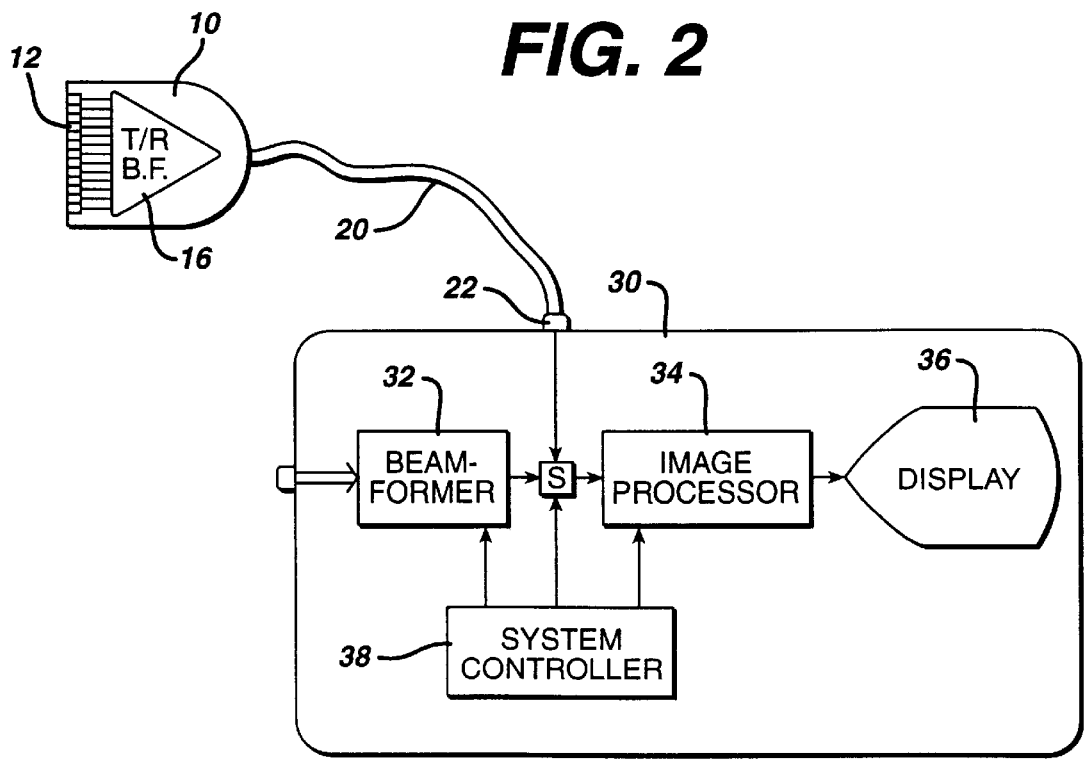
FIG. 2 illustrates an ultrasonic probe with an integral beamformer operatively connected to an ultrasonic imaging system.

FIG. 2 illustrates an ultrasound system in which the beamforming for both ultrasonic transmission and reception is done within the probe, significantly reducing the number of conductors needed within the cable 20. The elements of the transducer array 12 are coupled to a transmit/receive beamformer 16, which controls the timing, steering and focusing of the ultrasonic beams transmitted by the array and the beamforming of coherent echo signals from the signals received by the array elements. The formed beam, rather than signals from each transducer element, are coupled through the cable 20 for image processing and display by the ultrasound system 30. The cable 20 will also convey control information from the system controller 38 which commands the beamformer as to the specifics of the image being scanned. This control information can be conveyed by a serial digital line in the cable and the information stored in beamformer registers as discussed below. The cable will also carry supply voltages for the beamformer and the transducer array. Even when the transmit/receive beamformer 16 is a digital beamformer producing multibit digital data, the number of cable conductors is still substantially reduced as compared to the conductors required for a conventional 64, 96 or 128 element transducer array.

Since the received ultrasound beam is formed in the probe 10 in FIG. 2, the probe does not need to use the beamformer 32 in the ultrasound system 30. The beamformed echo signals produced by the probe 10 can be coupled directly to the image processor 34 for immediate processing and subsequent display. In the embodiment of FIG. 2 this is accomplished by a switch S which is switched under control of the system controller to connect the beamformed echo signals from probe 10 to the image processor, rather than signals produced by the system beamformer 32. As is conventional, a "personality chip" in the probe 10 or its system connector 22 notifies the user of the characteristics of the probe 10 and selection of probe 10 by the user at the user controls causes the system controller to command the probe to operate and connect its echo information to the image processor 34.

Figure 3:
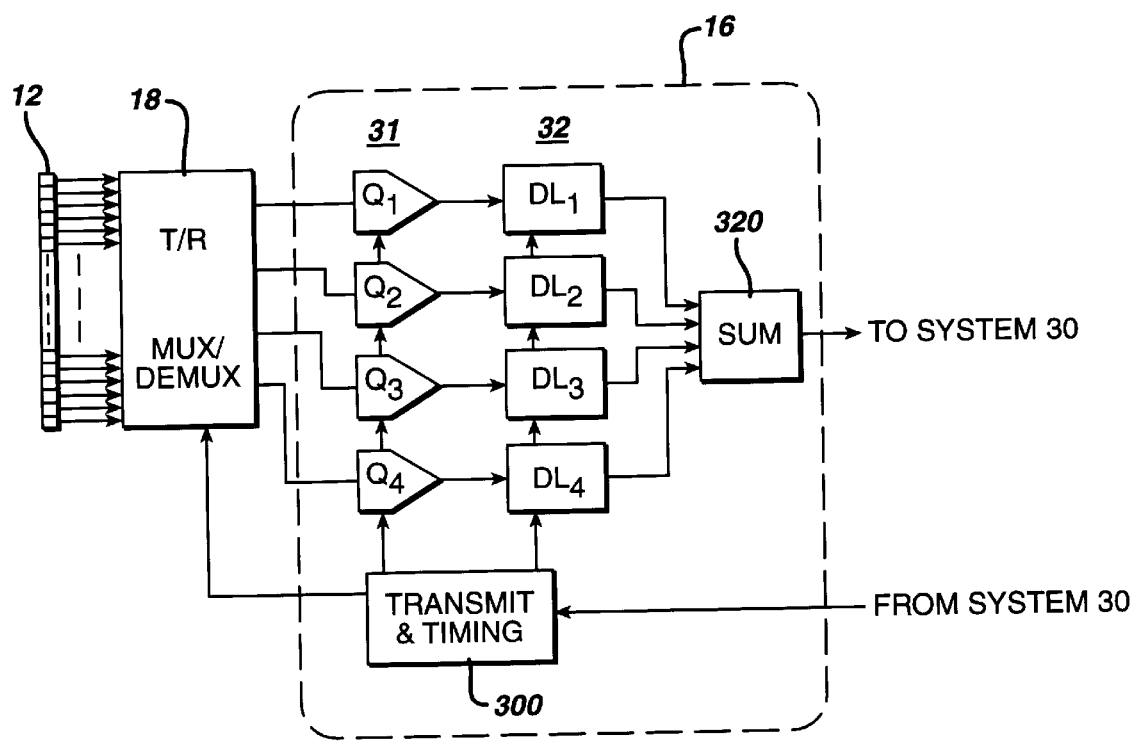
FIG. 3 is a more detailed block diagram of the ultrasonic probe of FIG. 2.

FIG. 3 illustrates an embodiment of an ultrasonic probe with a beamformer 16 and a transmit/receive multiplexer/demultiplexer 18. The beamformer 16 includes transmit and timing circuitry 300 which controls the timing of the ultrasonic waves transmitted by the elements of the transducer array 12. The transmit and timing circuitry receives command signals from the ultrasound system 30 to control the probe to produce the type of image desired by the user. The transmit and timing circuitry also directs the transmit/receive multiplexer/demultiplexer to select the desired active aperture of the array. The transmit and timing circuitry can also control the nature of the transmitted wave, for instance, transmitting different waves for B mode and Doppler imaging. The timing and control signals are applied to the multiplexer/demultiplexer 18 and elements of the array are excited at the proper times to steer and focus the desired transmit beam.

Echoes received by the array elements are converted to electrical signals by the elements and directed by the multiplexer/demultiplexer 18 to the receive beamforming circuitry of the beamformer 16. The received echo signals from the transducer elements of the active receive aperture are coupled to individual channels of the beamformer; the drawing of FIG. 3 illustrates a four channel beamformer. The preferred beamformer is fabricated in integrated circuit form and preferably will contain a multiple of four channels in each beamformer chip. Four, eight, or sixteen channel beamformer chips may readily be employed for most large element count arrays. The preferred beamformer is a sampled data beamformer which may use either sampled analog or digital technology. In either case each channel of the beamformer includes an initial quantizing stage 31 followed by a delay line stage 32. The outputs of the delay line stages are coupled to a summing circuit 320 which combines the delayed echo signals to form the receive beam. The four channel beamformer illustrated in FIG. 3 includes four quantizing stages $Q_1$, $Q_2$, $Q_3$, and $Q_4$ followed by four delay line stages $DL_1$, $DL_2$, $DL_3$, and $DL_4$. The coherent echo signals at the output of the summing circuit 320 are coupled to the ultrasound system 30 for image processing and display.

When the receive beamformer is of the sampled analog variety the quantizing stages comprise sample-and-hold circuits which sample the received echo signals at times indicated by the transmit and timing circuitry 300. The sampled analog signal voltages are then appropriately delayed by charge coupled device (CCD) bucket brigade delay lines as the delay line stages. The delay time is controlled by the transmit and timing circuitry 300 in any of several ways. One is to select one of a plurality of input taps to the CCD delay line to which the sampled voltage is applied. Another is to select one of a plurality of output taps from the stages of the CCD delay line to the summing circuit 320. In either case the selection of the tap will select the number of stages through which the voltage sample will be shifted and hence delayed. A third delay technique is to vary the frequency at which samples are shifted through the CCD stages: a lower frequency imparts a longer delay to the samples being shifted. The summed output signals may be digitized by an analog to digital converter in the probe and transmitted to the ultrasound system 30 in digital form, or the analog signals may be transmitted to the ultrasound system 30 and converted into digital echo samples in the ultrasound system. The latter approach would require only a single output signal conductor in the cable 20.

When the receive beamformer is a digital beamformer, the quantizing stages comprise analog to digital converters which convert the per element analog signals to digital samples at sampling times indicated by the transmit and timing circuitry 300. The digital echo samples are then digitally delayed by a digital delay line which can take the form of a random access memory, shift register, or digital FIFO register. The delay of each digital delay stage is controlled by the transmit and timing circuitry 300 which controls the write-read interval of a sample in memory or the shift frequency of a shift register or FIFO register. The delayed samples at the outputs of the digital delay lines are digitally summed and forwarded to the ultrasound system 30.

Figure 4:
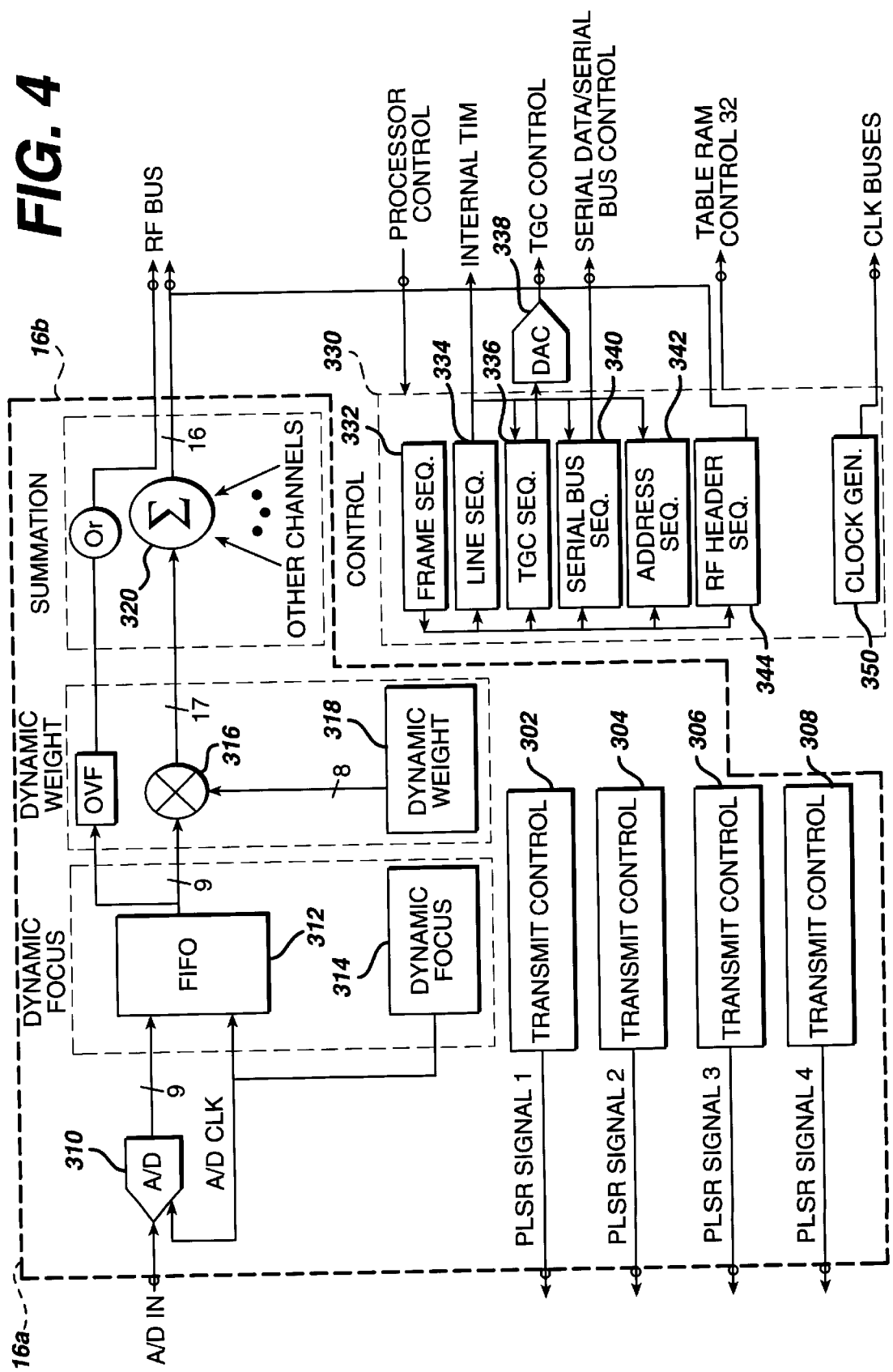
FIG. 4 illustrates in block diagram form a digital beamforming integrated circuit suitable for use in the ultrasonic probe of FIG. 3.

A digital beamformer suitable for use in the probe of FIG. 3 is shown in block diagram form in FIG. 4. This drawing shows one section 16a of a beamformer integrated circuit 16. There are eight such sections on the beamformer I.C. to provide beamforming of the signals of eight transducer elements from the multiplexer/demultiplexer 18. Each echo signal from the multiplexer/demultiplexer is coupled to the input of an A/D converter 310, where the echo signals are converted to digital data. The A/D converters are located on the same integrated circuit as the beamformer itself, which minimizes the external connection pins of the integrated circuit. Only one analog input pin is required for each beamformer channel, and only one set of digital output pins is required for the coherently summed output signal. The digital data from the A/D converter for each element (or each pair or group of elements in a folded or coarse aperture) is shifted into a first in, first out (FIFO) register 312 by a clock signal A/D CLK. The A/D CLK signal is provided by a dynamic focus controller 314 which defers the start of the clock signal to provide an initial delay, then controls the signal sampling times to provide dynamic focusing of the received echo signals. The length of the FIFO register 312 is determined by the transducer center frequency, the aperture size, the curvature of the array, and the beam steering requirement. A higher center frequency and a curved array will reduce the steering delay requirement and hence the length of the FIFO register, for instance. The delayed echo signals from the FIFO register 312 are coupled to a multiplier 316 where the echo signals are weighted by dynamic weight values provided by a dynamic weight controller 318. The dynamic weight values weight the echo signals in consideration of the effects of the number of active elements, the position of an element in the aperture, and the desired apodization function, as the aperture expands by the inclusion of additional outer elements as echoes are received from increasing depths along the scanline. The delayed and weighted echo signals are then summed with appropriately delayed and weighted echo signals from other elements and echo signals from any other delay stages which are coupled in cascade through a summer 320. The beamformed echo signals, together with synchronous overflow bits, are produced as output scanline data on an RF data bus. Accompanying each sequence of scanline echo signals is identifying information provided by an RF header sequencer on the I.C., which identifies the type of scanline data being produced. The RF header can identify the scanline as B mode echo data or Doppler data, for instance.

Other digital and sampled data storage devices can be used to provide the beamformer delays, if desired. A dual ported random access memory can be used to store the received digital echo samples, which are then read out from the memory at times or in sequences which provide the desired delay for the signals from the transducer elements.

Each section 16a of the beamformer I.C. includes transmit control circuits 302–308 for four transducer elements of the array. The eight sections of the I.C. thus provide transmit control for 32 elements of the array at the same time, thereby determining the maximum transmit aperture. The transmit control circuits produce waveforms of predetermined durations and periodicities which activate multiplexer pulsers at the appropriate times to produce a transmitted acoustic signal which is steered in the desired direction and focused at the desired depth of focus.

The beamformer I.C. 16 includes a common control section 330 which provides overall control for the transmission and receive functions of the eight beamformer channels on the I.C. The control section 330 is controlled by and receives data under control of the system controller 38 located in the ultrasound system 30. The control data tables for a particular image frame are stored in memory in the ultrasound system and are loaded into the control section 330 under command of the system controller. The control section 330 includes a number of sequencers for the probe's transmit and receive functions. The frame sequencer 332 produces information used by other sequencers which identifies the type of image frame which is to be produced. The frame sequencer may, for example, be loaded with data that defines the next frame as B mode scanlines interspersed between groups of four Doppler scanlines, and that the sequence of scanlines will be all odd numbered scanlines followed by all even numbered scanlines. This information is supplied to the line sequencer 334, which controls the timing required to acquire the desired scanlines. During the scanline acquisition the line sequencer controls the TGC sequencer 336 so that it will produce the desired sequence of TGC control data. The TGC control data from the TGC sequencer is converted to a voltage signal by a digital to analog converter (DAC) 338 and applied to the TGC control input terminal(s) of the multiplexer/demultiplexer 18. The address sequencer 342 controls the loading of data for a new scanline into various realtime registers of the beamformer such as the registers of the TGC sequencer, the dynamic focus 314 and dynamic weight controllers 318, and the serial bus sequencer 340, which produces serial data on a serial bus for control registers of the multiplexer/demultiplexer 18. All registers on the beamformer I.C. which perform real time functions are double buffered. The registers of the transmit/receive multiplexer/demultiplexer 18 are also double buffered so that control data for multiplexing and TGC control can be put on the serial bus and loaded into multiplexer/demultiplexer registers during the line preceding the scanline for which the control data is used.

The beamformer I.C. includes in its control section a clock generator 350 which produces a plurality of synchronous clock signals from which all operations of the probe are synchronized. A crystal oscillator (not shown) is coupled to the beamformer I.C. 16 to provide a basic high frequency such as 60 MHz from which all of the clock signals of the probe may be derived.

Further details on the operation of the beamformer I.C. and its sequencers may be found in U.S. Pat. No. 5,817,024.

Figure 5:
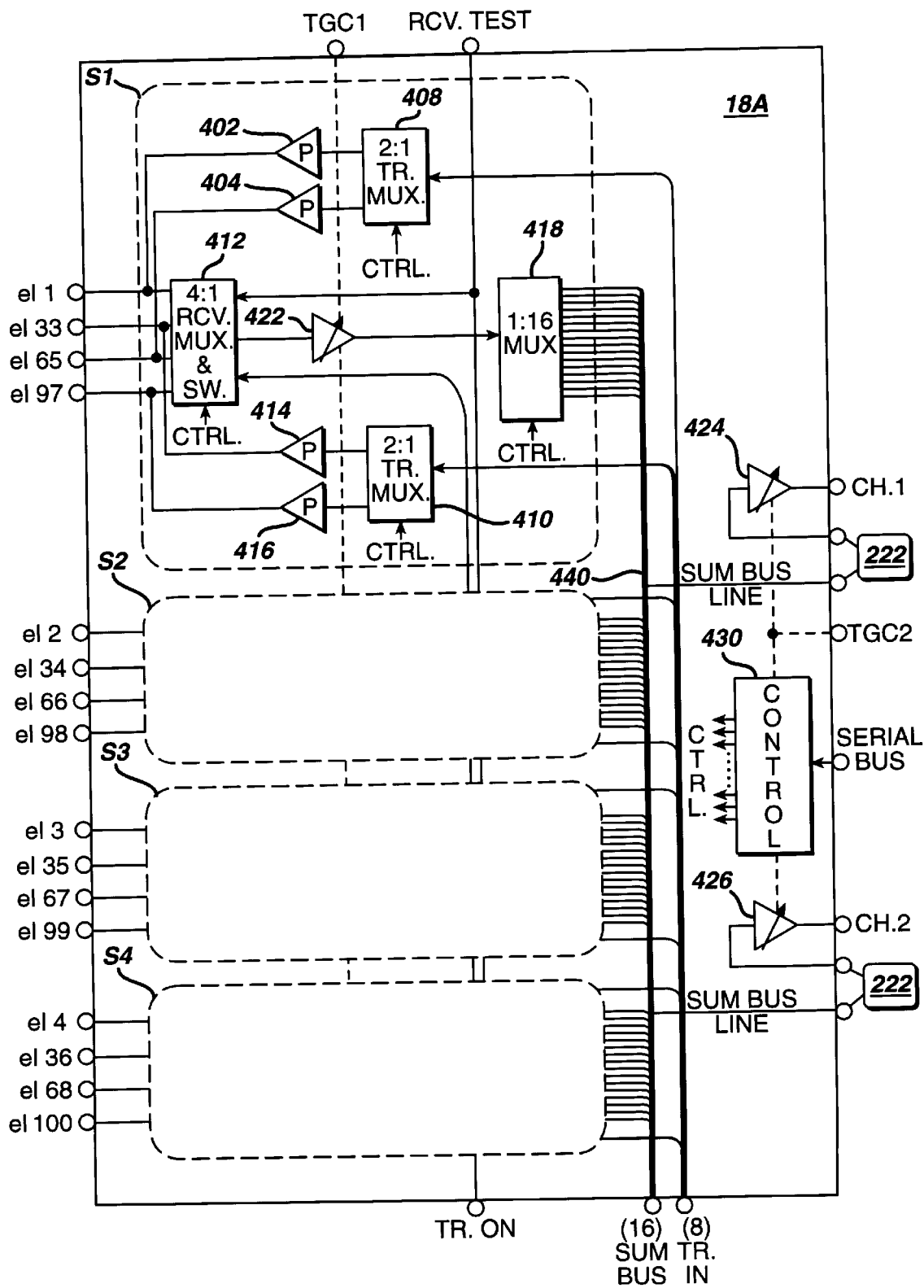
FIG. 5 illustrates in block diagram form a multiplexer suitable for use in the ultrasonic probe of FIG. 3.

A transmit/receive multiplexer I.C., suitable for use as multiplexer/demultiplexer 18 in the probe of FIG. 3, is shown in FIG. 5. The signal paths of the multiplexer I.C. 18A are divided into four identical sections S1, S2, S3, and S4. In this drawing section S1 is shown in internal detail. The section S1 includes two 2:1 transmit multiplexers 408 and 410, each of which is responsive to a pulser signal on one of eight Transmit In lines. Each 2:1 transmit multiplexer has two outputs which drive pulsers 402, 404, and 414, 416, the outputs of which are coupled to multiplexer I.C. pins to which transducer elements are connected. In the illustrated embodiment the 2:1 transmit multiplexer 408 is coupled to drive either element 1 or element 65, and the 2:1 transmit multiplexer 410 is coupled to drive either element 33 or element 97. The 2:1 transmit multiplexers of the other sections of the multiplexer I.C. 18A are each similarly coupled to four transducer elements. With a separate pulser for each transducer element, the multiplexer I.C. 18A can independently and simultaneously drive eight of the sixteen transducer elements to which it is connected.

The transducer element pins to which the pulsers of each section are coupled are also coupled to the inputs of a 4:1 receive multiplexer and switch 412. When the pulsers are driving the transducer elements during ultrasound transmission, a signal on a Transmit On line which is coupled to all of the 4:1 Receive Multiplexers and Switches on the multiplexer I.C. switches them all into a state which presents a high impedance to the high voltage drive pulses, thereby insulating the rest of the receive signal paths from these high voltage pulses. All of the 4:1 receive multiplexers and switches of the multiplexer I.C. are also coupled to a Receive Test pin of the multiplexer I.C., by which a test signal can be injected into the receive signal paths and propagate through the receiver system. During echo reception each 4:1 receive multiplexer and switch couples the signals of one of the four transducer elements to which it is coupled to a 1:16 multiplexer 418 by way of a first TGC stage 422. The gain of the first TGC stages on the multiplexer I.C. is controlled by a voltage applied to a TGC1 pin of the multiplexer I.C. which, in a constructed embodiment, comprises two pins for application of a differential control voltage. The 1:16 multiplexers of each section of the multiplexer I.C. each route received echo signals to one of the sixteen lines of a Sum Bus 440. Two of the sixteen Sum Bus lines are shown at the right side of the drawing, and are coupled to filter circuits 222. The filtered bus signals are coupled to input pins leading to two second TGC stages 424 and 426, the gain of which is controlled by the voltage applied to one or two TGC2 pins. The outputs of these second TGC stages in the illustrated embodiment are connected to output pins leading to channels of the probe's beamformer I.C.

The multiplexer I.C. 18A also includes a control register 430 which receives control signals over a serial bus from the beamformer I.C. The control register distributes control signals to all of the multiplexers of the multiplexer I.C. as shown by the Ctrl. input arrows.

Constructed embodiments of the multiplexer and beamformer I.C.s will have a number of pins for supply and bias voltages and ground connections and are not shown in the drawings.

It will be appreciated that only a few conductors are needed in the probe cable in the embodiments of FIGS. 2–5 since the numerous conductors for individual transducer elements are replaced by conductors for the beamformer control data, the beamformed output signals and supply voltages for the transducer, beamformer and multiplexer I.C.s. A typical CCD embodiment can require a conductor for the CCD beamformer output signals, a serial data line providing control data from the ultrasound system to the transmit and timing circuitry 300, DC supply voltages and reference conductors for the beamformer and multiplexer I.C.s, and a drive voltage as required to drive the piezoelectric material during ultrasound transmission. The digital beamformer embodiment would replace the CCD output conductor with a number of conductors equal to the number of bits in a beamformed data word (for parallel transmission) or a serial data line if the beamformed words are being sent to the ultrasound system as serial data. Parallel output data, while requiring more conductors in the cable, affords a worthwhile improvement in axial resolution and eliminates the need for a serial to parallel converter in the ultrasound system.

The present inventors have discovered that since an ultrasound probe of the present invention is producing beamformed scanline samples as output signals rather than individual signals from a large number of transducer elements, the volume of data produced by the probe is at a level which will permit wireless transmission of the probe's output signals to the ultrasound system. A transmitter bandwidth of 4 M bits per second is sufficient to transfer ultrasound images without compression at a frame rate of nearly 15 Hz, suitable for real time image display. I.C. transmitter bandwidths today are in the range of 11 MBPS, and are expected to be in the range of 25 MBPS in a few years. Additionally, by the use of data compression, the number of bits per B mode ultrasound image, around 250,000 bits per image, can be reduced with minimal decrease in image quality by data compression factors ranging from 4 to 20, affording greater frame rates. An embodiment of the present invention which provides this cable-less connection to an ultrasound system is shown in FIGS. 6a and 6b.

Figure 6A:
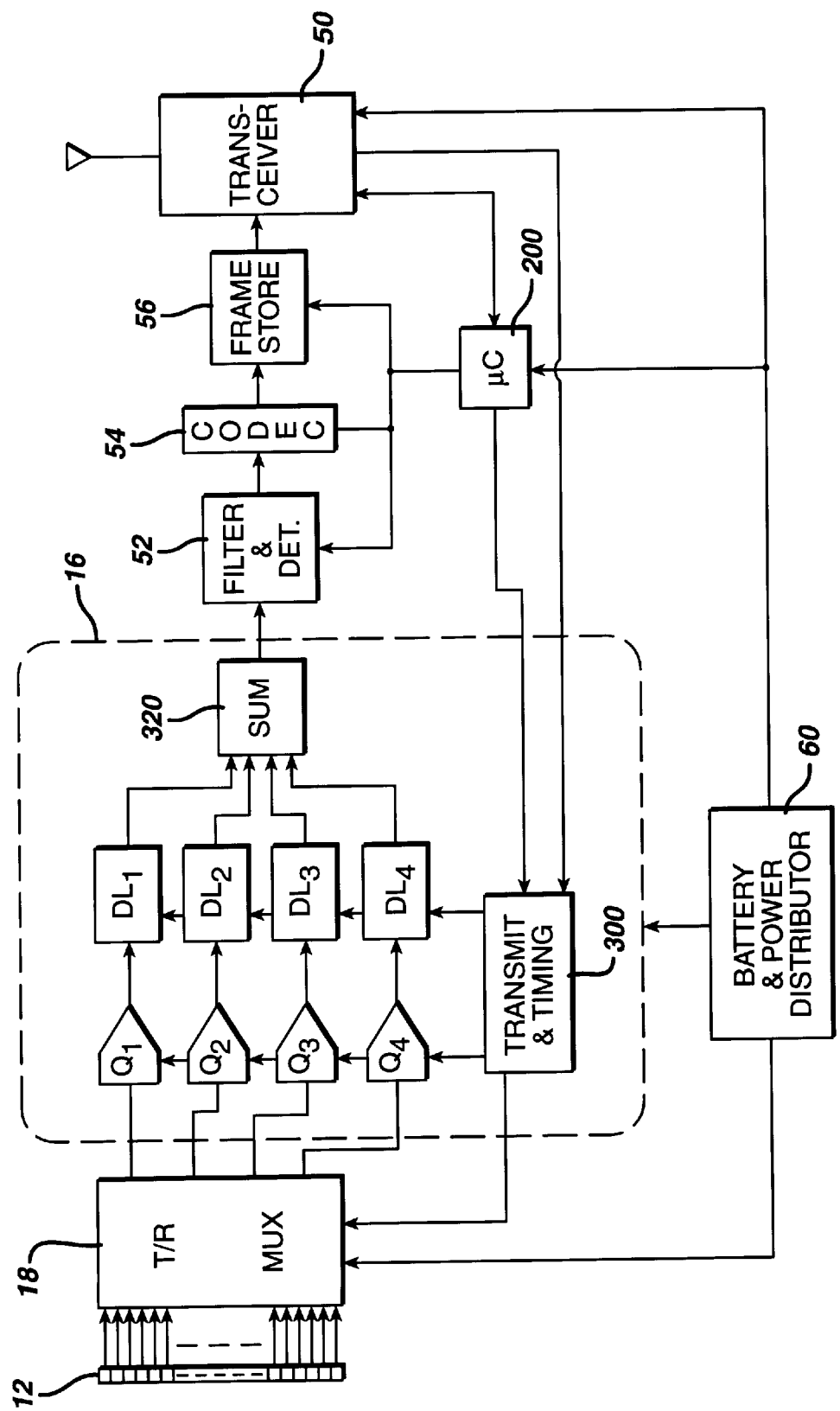
FIGS. 6a and 6b illustrate a cable-less ultrasonic probe and an associated ultrasonic imaging system in accordance with the principles of the present invention.
Figure 6B:
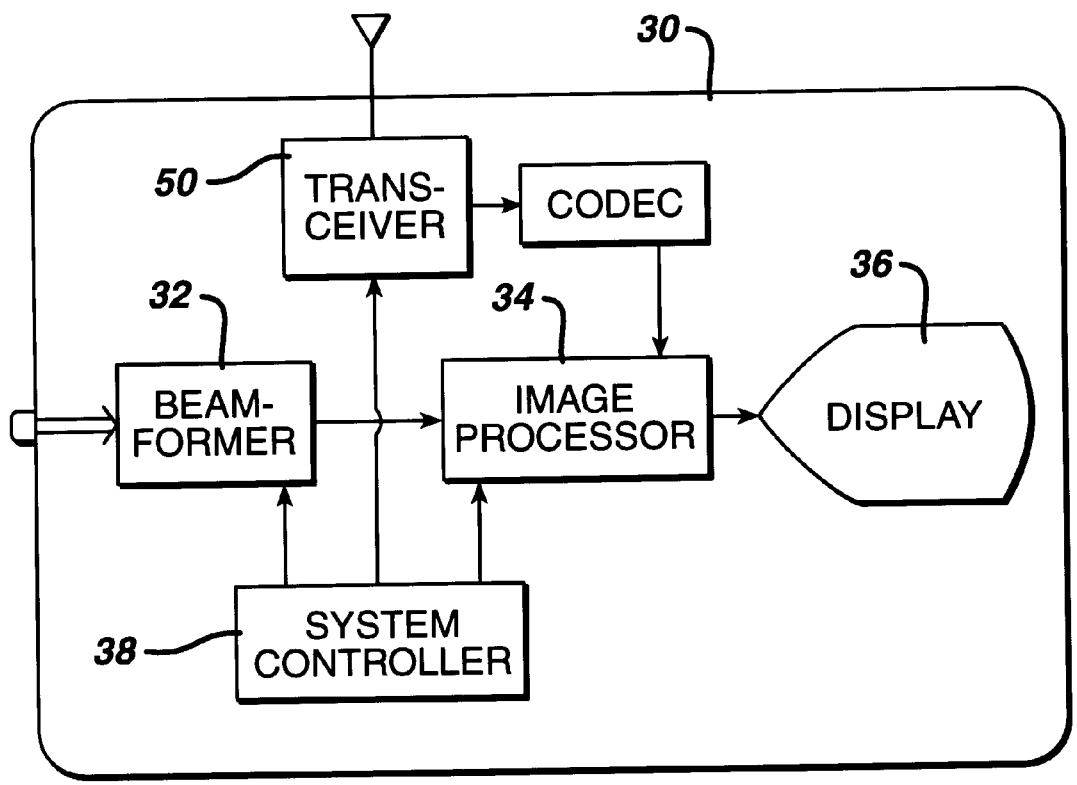

In FIG. 6a the probe of FIG. 3 includes several additional elements coupled to the beamformer 16, a digital signal processor 52 which performs filtering and detection, a compression/decompression circuit (CODEC 54) which compresses the beamformed data, a double buffered frame store 56, and a transceiver 50 which communicates with a similar transceiver in the ultrasound system 30. These elements are operated under control of a microcontroller 200 which controls the processing and transmission of data to and from the ultrasound system. Useful as microcontrollers are processors such as the Intel 80186 processor and comparable contemporary processors available from vendors such as Hitachi and Intel. The transceiver 50 receives control data from the ultrasound system to control the type of ultrasound image being produced, such as a B mode or Doppler image, and the size of a Doppler window in a colorflow image, for instance. As this control data is received it is coupled to the transmit and timing circuitry 300 to control the scanning performed by the probe.

The scanline data produced by the summer 320 is coupled to the digital signal processor 52 which performs filtering and, optionally, detection. The DSP 52 can also perform Doppler processing as described in the aforementioned U.S. patent. The filtering performed can be either lowpass or bandpass filtering which removes sampling frequency signal components from the beamformed signals. Preferably this filtering is implemented by multiplier-accumulators performing quadrature bandpass filtering (QBPs). As described in U.S. patent application Ser. No. 08/893,426, such an implementation advantageously performs three functions: bandlimiting the beamformed signals, separating the signals into quadrature (I and Q) pairs, and decimating the sampling rate. In a preferred embodiment the transducer signals are oversampled by the quantizing stages of the beamformer in relation to the Nyquist criterion. Oversampling permits the filtering of the beamformed signals by decimation filtering which both imposes a filter characteristic on the signals and reduces the data rate. The reduced data rate has the benefit of lessening the data transfer requirement for the transceiver in a wireless probe.

B mode signals can be detected in the DSP by taking the square root of the sum of the squares of the I and Q samples. For Doppler signals the I and Q data can be wall filtered by the DSP and, through storage of a group of received scanlines forming a Doppler ensemble, Doppler frequency estimation can be performed at sample volume points along each scanline. The ultrasound signal data may be compressed if desired by the CODEC 54 and is stored temporarily in the frame store 56. At the time when the microcontroller 200 determines that the ultrasound data is to be transmitted to the ultrasound system 30, the data is coupled to the transceiver 50 for transmission back to the ultrasound system for image processing and display. Since image processing including scan conversion is performed in the ultrasound system, the scanlines are transmitted to the ultrasound system in unscanconverted form, e.g., R-$\theta$ format. The image processor 34 in the ultrasound system converts the R-$\theta$ scanline data to the desired display format.

Since the cable-less probe of FIG. 6a does not receive power by the usual cable, the probe must be battery powered. A battery and power distributor subsystem 60 is shown as a component of the probe. The subsystem 60 preferably uses rechargeable lithium ion batteries and produces supply voltages for the circuitry and transceiver of the probe and the requisite excitation voltage for the piezoelectric elements of the transducer array. Techniques for recharging the battery from the ultrasound system are described in concurrently filed application Ser. No. 09/196,852, entitled "ULTRASONIC DIAGNOSTIC IMAGING SYSTEM WITH CORDLESS SCANHEAD CHARGER."

The ultrasound system 30 of FIG. 6b includes a transceiver 50 for the transmission of scan control data to the probe of FIG. 6a and for the reception of ultrasonic image data from the probe. The scan control data is provided to the system transceiver 50 by the system controller 38. The received image data bypasses the beamformer 32 in the ultrasound system since it has already been beamformed in the probe, and is applied directly to the image processor 34 for image processing and display.

Figure 7A:
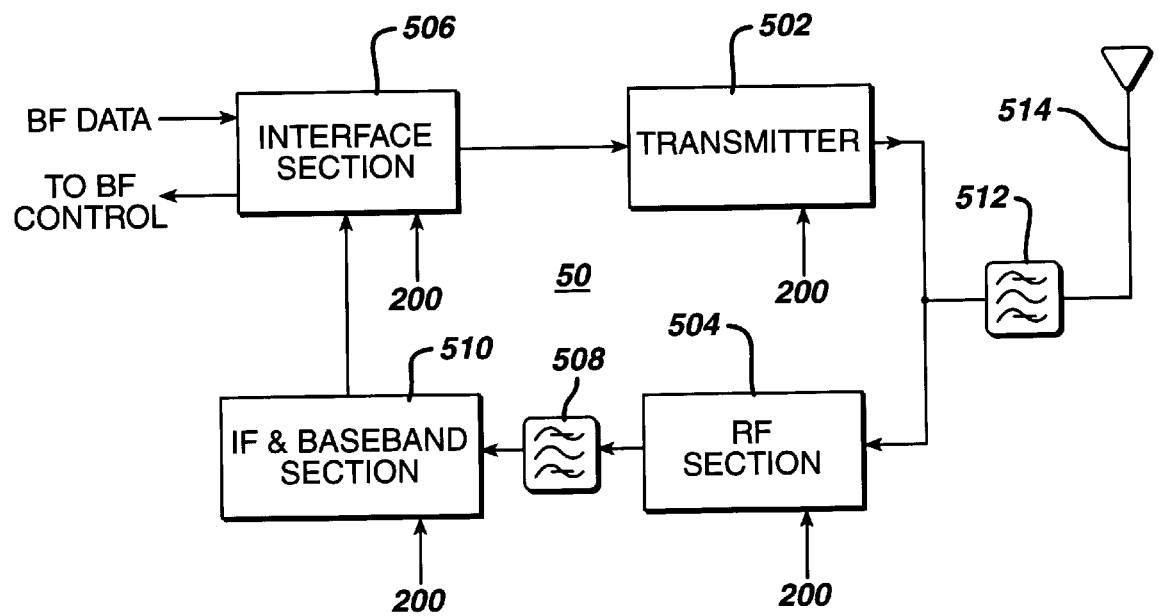
FIGS. 7a–7d illustrate transceiver configurations suitable for use with the ultrasonic probe of FIG. 6a and the ultrasound system of FIG. 6b.
Figure 7B:
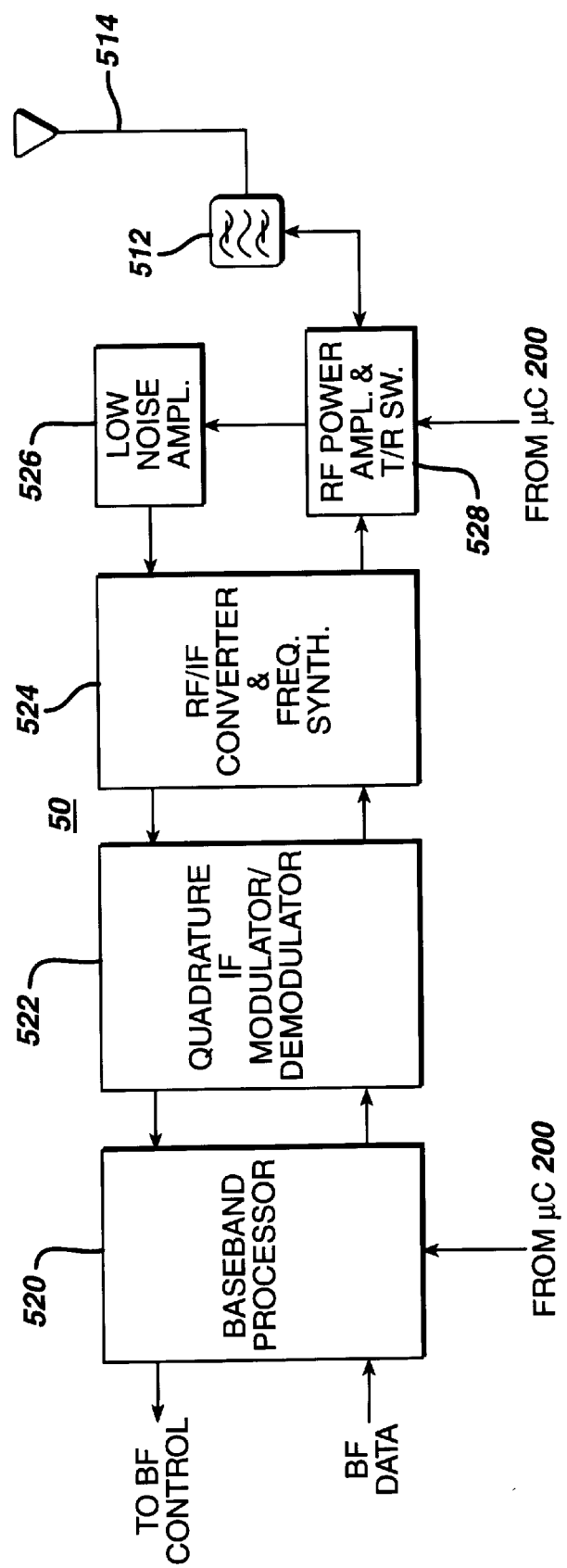

Transceiver configurations suitable for use in the probe of FIG. 6a are shown in FIGS. 7a and 7b. In the transceiver of FIG. 7a an interface section 506 synchronizes and interfaces beamformer data for transmission, and likewise interfaces received beamformer control data for the transmit and timing circuitry 300. Beamformer data which is to be transmitted is coupled to a UHF transmitter 502 which modulates the data and couples an r.f. transmit signal by way of a bandpass filter 512 to an antenna 514 where the signal is transmitted. Received r.f. signals are filtered by the bandpass filter 512 and coupled to an RF receiver section 504 where the signals are amplified and coupled by a bandpass filter 508 to an IF & baseband receiver section 510 where the signals are demodulated and detected. The received signals are coupled by the interface section 506 to the control circuitry for the beamformer 16. Operation of the separate sections of the transceiver of FIG. 7a is controlled by control signals and commands from the microcontroller 200.

An alternate transceiver configuration is shown in FIG. 7b. In this arrangement beamformer data is applied to a baseband processor 520 which synchronizes and formats packets of beamformer data for transmission. The beamformer data is modulated by a quadrature IF modulator/demodulator 522 and the modulated data is coupled to an RF/IF converter & frequency synthesizer 524 which produces a low level r.f. signal. The r.f. signals are amplified and coupled by an RF power amplifier and transmit/receive switch 528 to bandpass filter 512 and antenna 514. Received control signals are filtered by the bandpass filter 512 and coupled and amplified by the RF power amplifier and transmit/receive switch 528 to a low noise amplifier 526. The received and amplified r.f. signals are demodulated to intermediate frequency signals by the RF/IF converter & frequency synthesizer 524 and further demodulated to baseband by the quadrature IF modulator/demodulator 522. The baseband signals are sampled and interfaced to other probe components by the baseband processor 520 where the received signals control the transmission and timing of the probe's transducer array 12.

Components suitable for use in the transceiver configuration of FIG. 7a are available from Telefunken Semiconductors of Germany, including the TEMIC U4311B-C RF transmitter I.C. and associated components. Components suitable for use in the transceiver configuration of FIG. 7b are available from Harris Semiconductor of Melbourne, Fla., USA including components of the Harris Prism™ wireless chip set, which are suitable for use in spread spectrum applications in the range of 2.4 GHz in keeping with the IEEE802.11 standards and with data throughputs currently up to 11 MB/sec. Spread spectrum technology is desirable for a wireless probe because the radiated energy is spread over a broad frequency range, reducing possible interference with other devices in the medical environment. Such transmission can be safely used near pacemakers and other sensitive medical devices.

The same transceiver configurations can be used in the ultrasound system 30 of FIG. 6b, with appropriate reversal of the transmitted and received data paths.

Figure 7C:
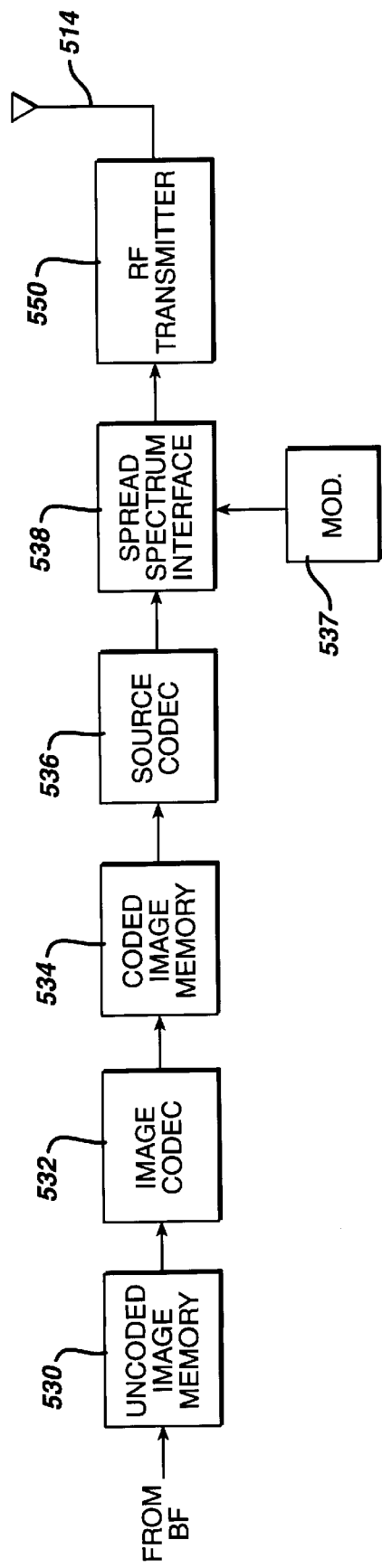
Figure 7D:
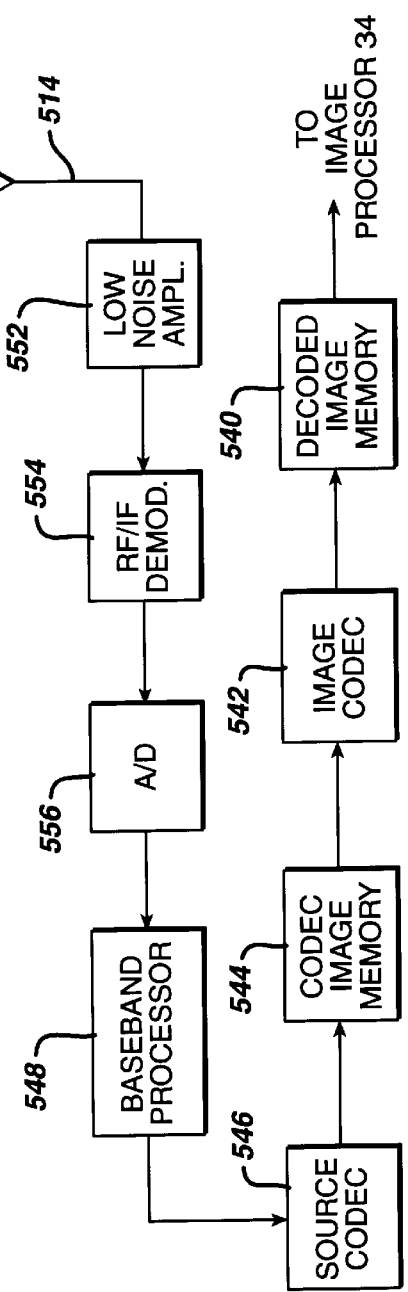

Another transmitter-receiver configuration suitable for use in the probe and ultrasound system of FIGS. 6a and 6b is shown in FIGS. 7c and 7d, which illustrate further details of useful compression techniques. This configuration is capable of implementing several compression schemes, including JPEG, MPEG and wavelet compression techniques. JPEG is an intraframe compression technique which operates on the image data of a single image. In JPEG compression an image is divided into numerous blocks of image data which undergo a cosine transformation to produce coefficient data. The coefficient data is quantized and encoded by a Huffman code to produce encoded image coefficient data. MPEG is an interframe technique which operates on sequential image frames. The changes in image data from frame to frame are encoded by motion compensated predictive coding, and the coded change data is used to reconstruct an updated image from a previous image by applying changes from one frame to the next.

Intraframe and interframe compression can be implemented using wavelet techniques. In intraframe wavelet compression the image data is divided into two dimensional blocks of data which undergo complementary highpass and low pass filtering in various combinations, producing coefficient data. The wavelet coefficients are then quantized and encoded to accomplish various degrees of compression. Higher compression ratios can be achieved by the use of interframe wavelet transformation on a sequence of images. In interframe wavelet compression the complementary wavelet filters operate on the image sequence in both spatial and temporal dimensions. The three dimensional image data is filtered, quantized and encoded. To decode the compressed image, the encoded data is processed using a technique which is the inverse of the encoding process such that the encoded data can be reconstructed into an image or an image sequence. These techniques can yield data compression ranging from 2–4:1 for JPEG compression to 100:1 for spatial-temporal wavelet compression, thereby significantly reducing the data throughput required of the transmission system.

In most ultrasonic imaging systems the image data lines are acquired relatively sparsely in relation to the image spatial dimensions when higher image rates are employed, which are limited by the velocity of sound in tissue. For example 128 lines may be acquired over a 90° sector image. To form a completely filled out image, missing image data is interpolated between the acquired image lines. Generally such interpolated data is added during the scan conversion process. The interpolated image data carries little new information since they are derived from the acquired image data. Hence, for a wireless probe, it is preferable to transmit image data prior to scan conversion and interpolation in order to minimize the required transmission bandwidth required. With data compression the bandwidth requirements can be even further reduced.

In FIG. 7c image data from the beamformer 16, which may be filtered and detected data, is temporarily stored in an uncoded image memory 530. The memory 530 holds all of the image lines of an image frame so that the compression technique can operate on a full frame of image data. The image data is then encoded by an image CODEC 532 which performs the coding of the selected compression technique. The image CODEC 532 may perform intraframe spatial encoding for JPEG compression, interframe or intraframe spatial encoding for MPEG compression, or interframe or intraframe spatial and temporal encoding for wavelet compression. The coefficients resulting from JPEG compression or data encoded by one of the other techniques is stored in a coded image memory 534. The coded data then undergoes final compression processing in a source CODEC 536. For JPEG compression this processing would include quantizing the coefficient data and source encoding by conversion of the coefficients into Huffman code. The compressed data then undergoes spread spectrum processing in a spread spectrum interface 538 which performs frequency domain or time domain spread spectrum processing. In this processor the compressed data is divided by frequency or time division into data transmission units. The spread spectrum data is modulated onto a carrier signal by a modulator 537 which performs superhetrodyne modulation of the data to be transmitted. The modulated data is transmitted from an antenna 514 by an RF transmitter 550.

FIG. 7*d* shows the elements of the receiving and decompression processor in the ultrasound system 30, where the modulation and compression of the transmitter is reversed. RF signals received by an antenna 514 are amplified by a low noise amplifier 552 and demodulated by an RF/IF demodulator 554. The demodulated signals are converted to digital data by and A/D converter 556 and coupled to a baseband processor 548. The baseband processor reconstructs the spread spectrum produced by the spread spectrum interface 538 of the transmission sequence. The reconstructed spectrum data is coupled to a source CODEC 546, which in the case of JPEG compression performs Huffman code decoding, the inverse of the source CODEC 536. Alternately, the source CODEC performs the inverse of the source CODEC processing for the other compression techniques. The data produced by the source CODEC is temporarily stored in a coded image memory 544 and is then applied to an image CODEC 542. The CODEC 542 performs the inverse operation of the image CODEC 532 and decodes the coefficient data or other encoded data stored in the coded image memory, restoring the original image data. The image data is stored in a decoded image memory 540, from which it is coupled to the image processor 34 of the ultrasound system 30 for further processing and display.

It will be understood that for duplex operation both the probe and the ultrasound system will perform both transmission and reception and hence will perform all of the operations of FIGS. 7*c* and 7*d*.

It will be appreciated that a free-running, unsynchronized probe can also be constructed in accordance with the present invention, whereby the transmit and timing circuitry of the probe executes one or more control sequences stored in the probe. A user would turn on the power of the probe and then select by buttons or switches on the probe the desired scanning sequence if more than one were available. The transceiver of the probe 10 could then operate as simply a transmitter, continually transmitting the image data back to the ultrasound system for processing and display until the probe were either de-selected or turned off. Such an arrangement would require only a one-way transmission path between the probe and the ultrasound system, as control data would not be transmitted from the ultrasound system. While affording a degree of simplicity in design, such an arrangement limits the user's ability to control scanning to that which is available from the controls located on the probe itself. Controls which are operated on the ultrasound system, such as the setting of multiple focal zones next to the displayed image or the placement of a desired Doppler window on a colorflow image, would not be effective in a one-way transmission embodiment. To make full use of the user interface (controls) of the ultrasound system and to minimize the control complexity of the probe, two-way communication is preferred, either simplex operation whereby the probe and ultrasound system alternately communicate with each other in a sequential fashion, or full duplex operation whereby the probe and ultrasound system can continuously communicate with each other simultaneously.

Another capability which two-way communication provides is the ability to regulate the transmitted power expended by the probe, a useful feature for a battery powered device. The strength of the signals received from the probe by the ultrasound system is measured and transmit level control signals sent back to the probe from the ultrasound system in a wireless feedback arrangement. These feedback signals instruct the probe to increase or decrease its radiated energy in accordance with the quality of the signals received from the probe and the distance between the probe and system receiver. Thus, the probe transceiver will transmit signals which are minimally sufficient for high quality reception by the ultrasound system over the distance between the probe and the system receiver, thereby minimizing the use of battery power by the probe transceiver. A similar feedback arrangement from the probe to the ultrasound system can be used by the ultrasound system to minimize its radiated energy and hence the risk of r.f. electrical interference with other devices in the medical environment.

The ultrasonic image data that is transmitted from the probe to the ultrasound system can be transmitted in packets, or blocks of data, which are preceded and followed by headers and trailers providing information concerning the characteristics of the ultrasound data. Preferably the transmitted data is grouped into sequences of scanline data, and a plurality of scanlines for an image frame are transmitted in a sequence which is preceded and followed by frame headers and trailers. The transmitted data may also be accompanied by communication protocol headers and trailers identifying the transmission format. The header information may include information identifying the probe, the type of compression employed in the transmission, and operating data such as probe temperature and other safety information. Such formatting protocols for a cordless scanhead are described more fully in concurrently filed application Ser. No. 09/197,186, entitled "ULTRASONIC DIAGNOSTIC IMAGING WITH CORDLESS SCANHEAD TRANSMISSION SYSTEM."

Figure 8A:
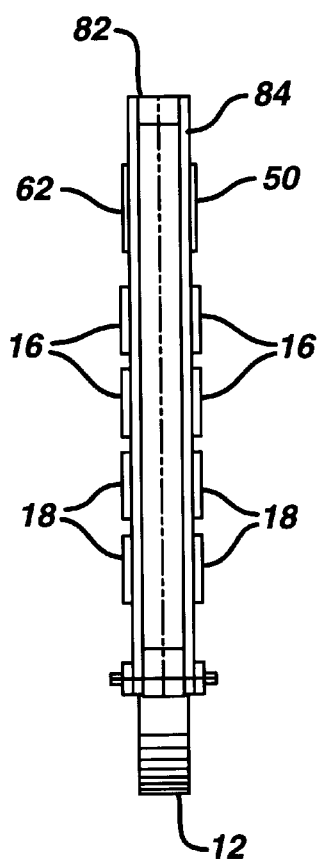
FIGS. 8a and 8b illustrate the internal array and integrated circuit packaging of a cable-less probe.
Figure 8B:
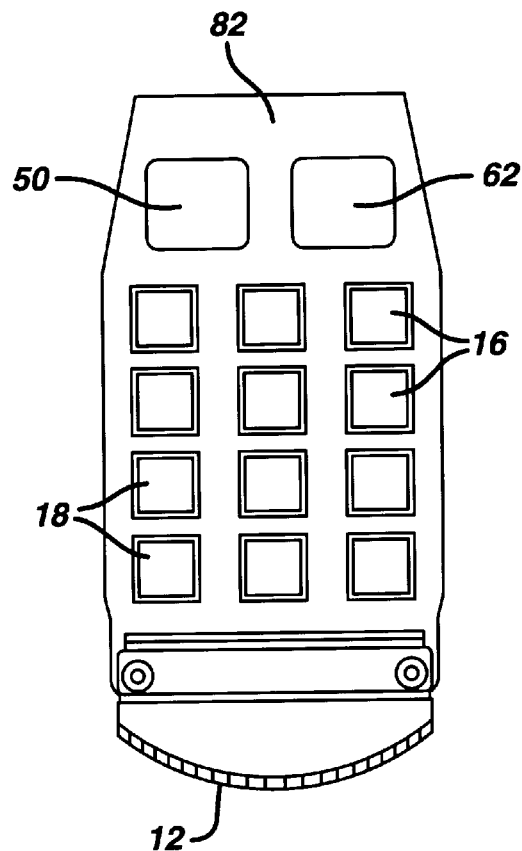

Assembly drawings for a cordless ultrasound probe are shown in FIGS. 8*a*, 8*b*, 9*a*, 9*b*, 9*c* and 9*d*. FIGS. 8*a* and 8*b* are side and plan views, respectively, of the inner components of a cordless ultrasound probe. Two printed circuit boards 82 and 84 are connected in a parallel sandwich arrangement as shown in FIG. 8*a*. The integrated circuits 18 for the multiplexer and for the beamformer 16 are mounted on the printed circuit boards. A transducer array module 12 is mounted at one end of the printed circuit boards and the elements of the array are connected to the multiplexer I.C.s. The number of multiplexer and beamformer I.C.s used will be determined by the number of elements of the transducer array and the desired active aperture during transmission and reception. For example, eight multiplexer I.C.s may be used for a 128 element array when each multiplexer I.C. is capable of connecting to sixteen elements as is the multiplexer I.C. of FIG. 5. Eight beamformer I.C.s, each with eight receive channels, may be used when a 64 channel receive beamformer is desired. Behind the multiplexer and beamformer I.C.s in FIG. 8*b* are the transceiver and power distribution circuits 50 and 62.

Figure 9B:
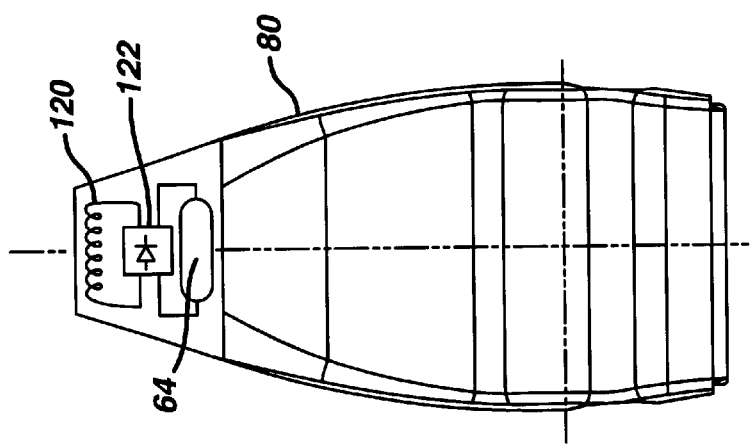
FIGS. 9a–9d illustrate the probe case for the components of FIGS. 8a and 8b.
Figure 9C:
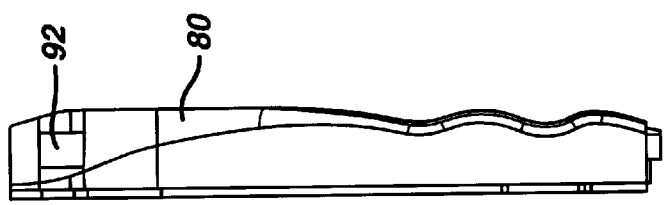
Figure 9D:
Figure 9A:
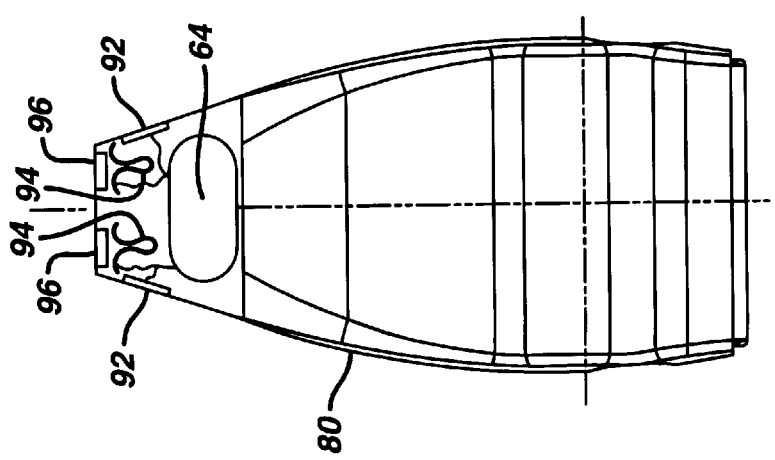

The assembled printed circuit boards and transducer module are mounted in a case 80, one half of which is shown in FIG. 9*a*. The lower end of the case in the drawing has a separate cap piece (not shown) which fits over the transducer array module and forms an acoustic window in front of the array. The printed circuit board is connected to a battery 64 which is located in the upper end (back) of the case 80. The terminals of the battery 64 are connected to external charging contacts 92 which are flush mounted on each side of the case 80 as shown in the plan view of FIG. 9*a* and the side view of FIG. 9*b*. Alternatively, the probe may employ internal charging contacts, here shown as spring contacts 94 in FIG. 9*a*. Access to the spring contacts may be by a movable cover or door over each spring contact, but in FIGS. 9*a* and 9*b* access to the spring contacts is provided by two rubber gaskets 96, one of which is shown in FIG. 9*d*. Each gasket has a self-sealing slit 98 through which battery charging pins may be inserted to access the spring contacts 94. As the battery charging pins force their way through the slits in the gaskets, a wiping action takes place to wipe away any excessive gel or other substances which may be present on the charging pins, thereby leaving the gel and other contaminants on the outside of the probe.

What is claimed is:

1. An ultrasonic probe which wirelessly communicates with an ultrasonic diagnostic imaging system for display of ultrasonic information acquired by said probe, comprising:
   a multielement transducer array which transmits beams of ultrasonic energy and receives ultrasonic echo signals;
   transmit timing control circuitry coupled to said transducer array to control the transmission of electronically steered and/or focused ultrasound beams by said transducer array; and
   a wireless transmitter, coupled to said transducer array, which transmits echo signal information,
   wherein said ultrasound system includes a wireless receiver for receiving said transmitted echo signal information.

2. An ultrasonic probe which wirelessly communicates with an ultrasonic diagnostic imaging system for display of ultrasonic information acquired by said probe, comprising:
   a multielement transducer array;
   a receive beamformer, coupled to said transducer array, which selectively combines echo signals received by elements of said transducer array to form beamformed echo signals; and
   a wireless transmitter, coupled to said receive beamformer, which transmits beamformed echo signals,
   wherein said ultrasound system includes a wireless receiver for receiving said transmitted beamformed echo signals.

3. An ultrasonic probe which wirelessly communicates with an ultrasonic diagnostic imaging system for display of ultrasonic information acquired by said probe, comprising:
   a multielement transducer array which transmits beams of ultrasonic energy and receives ultrasonic echo signals;
   transmit timing circuitry coupled to said transducer array to control the transmission of electronically steered and/or focused ultrasound beams by said transducer array;
   a receive beamformer, coupled to said transducer array, which selectively combines echo signals received by elements of said transducer array to form beamformed echo signals; and
   a wireless transmitter, coupled to said transducer array, which transmits echo signal information,
   wherein said ultrasound system includes a wireless receiver for receiving said transmitted echo signal information.

4. The ultrasonic probe of claim 1, 2 or 3, wherein said ultrasound system further includes a display for displaying ultrasonic images formed from the echo signal information transmitted by said wireless transmitter.

5. The ultrasonic probe of claim 1, 2 or 3, wherein said wireless transmitter comprises an r.f. transmitter, and wherein said wireless receiver comprises an r.f. receiver.

6. The ultrasonic probe of claim 1 or 3, wherein said ultrasound system further includes a probe control for controlling ultrasonic scanning by an ultrasonic probe, and wherein said probe further comprises:
   a wireless receiver which receives scanning control signals from said ultrasound system in response to operation of said probe control for operation of said transmit timing circuitry.

7. The ultrasonic probe of claim 6, wherein said receiver includes an IF section and a baseband section.

8. The ultrasonic probe of claim 7, wherein said receiver includes a quadrature demodulator.

9. The ultrasonic probe of claim 1, 2 or 3, wherein said transmitter has a transmitter bandwidth of at least 4 MBPS.

10. The ultrasonic probe of claim 9, wherein said transmitter has a transmitter bandwidth of at least 11 MBPS.

11. The ultrasonic probe of claim 1, 2 or 3, wherein said transmitter includes a superhetrodyne modulator.

12. The ultrasonic probe of claim 1, 2 or 3, wherein said echo signal information is transmitted as unscanconverted scanlines; and wherein said ultrasound system includes a scan converter for converting said scanlines to a desired image format.

13. The ultrasonic probe of claim 1, 2 or 3, wherein said transmitter comprises a UHF transmitter.

14. The ultrasonic probe of claim 1, 2 or 3, wherein said receiver includes an IF section and a baseband section.

15. The ultrasonic probe of claim 14 wherein said receiver includes a quadrature demodulator.

16. The ultrasonic probe of claim 1, 2 or 3, wherein said transmitter is a spread spectrum transmitter.

17. The ultrasonic probe of claim 1, 2 or 3, wherein said transmitter utilizes an r.f. transmit frequency in the range of approximately 2.4 GHz.

18. The ultrasonic probe of claim 1, 2 or 3, further comprising a data compression circuit for compressing echo signal information prior to its transmission by said transmitter.

19. The ultrasonic probe of claim 18, wherein said data compression circuit uses one of JPEG, MPEG or wavelet compression techniques.

20. The ultrasonic probe of claim 1, 2 or 3, wherein said transmitter includes a regulator which regulates the transmitted power as a function of either the quality of signals received by said ultrasound system or the distance between said probe and said ultrasound system.

21. The ultrasonic probe of claim 1, wherein said transmit timing control circuitry further comprises a pulse generator, having an input coupled to said transmit timing control circuitry and an output coupled to said multielement transducer array, which acts to pulse elements of said transducer array.

22. The ultrasonic probe of claim 21, wherein said transmit timing control circuitry is located on a digital integrated circuit.

23. The ultrasonic probe of claim 1, wherein said transmit timing control circuitry controls the transmission of ultrasound beams for B mode or Doppler imaging.

24. The ultrasonic probe of claim 1, wherein said transmit timing control circuitry further controls the active aperture of said transducer array.

25. The ultrasonic probe of claim 24, wherein said transmit timing control circuitry further includes a multiplexer coupled to the elements of said transducer array.

26. The ultrasonic probe of claim 25, wherein said multiplexer is located on an integrated circuit.

27. The ultrasonic probe of claim 1, wherein said probe further includes a data storage device for storing a transmit control sequence, wherein said transmit timing control circuitry executes said stored transmit control sequence to control the transmission of ultrasound beams by said transducer array.

28. The ultrasonic probe of claim 2 or 3, wherein said receive beamformer further includes a weighting circuit for applying a desired apodization function to received echo signals.

29. The ultrasonic probe of claim 2 or 3, further comprising time gain control (TGC) circuitry for applying a gain function to received echo signals as a function of depth from which said echo signals are received.

30. The ultrasonic probe of claim 2 or 3, wherein said beamformer comprises a sampled data beamformer.

31. The ultrasonic probe of claim 30, wherein said beamformer comprises a CCD beamformer.

32. The ultrasonic probe of claim 30, wherein said beamformer comprises a digital beamformer.

33. The ultrasonic probe of claim 2 or 3, further comprising a digital signals processor for performing one or more of: bandlimiting echo signal information; separating echo signals into quadrature signals; and decimating the sampling rate of echo signal information.

34. The ultrasonic probe of claim 2 or 3, further comprising a detector for detecting B mode echo information.

35. The ultrasonic probe of claim 2 or 3, wherein said receive beamformer includes a plurality of analog delays.

36. The ultrasonic probe of claim 35, wherein said analog delays comprise CCD delays.

37. The ultrasonic probe of claim 2 or 3, wherein said receive beamformer includes a plurality of digital delays.

38. The ultrasonic probe of claim 3, wherein said transmit timing circuitry controls the transmission of ultrasound beams for B mode or Doppler imaging.

39. The ultrasonic probe of claim 3, wherein said transmit timing circuitry further controls the active aperture of said transducer array.

40. The ultrasonic probe of claim 39, wherein said transmit timing circuitry further includes a multiplexer coupled to the elements of said transducer array.

41. The ultrasonic probe of claim 3, wherein said probe further includes a data storage device for storing a transmit control sequence, wherein said transmit timing circuitry executes said stored transmit control sequence to control the transmission of ultrasound beams by said transducer array.

42. The ultrasonic probe of claim 3, wherein said transmit timing circuitry further comprises a pulse generator, having an input coupled to said transmit timing circuitry and an output coupled to said multielement transducer array, which acts to pulse elements of said transducer array.

43. The ultrasonic probe of claim 3, wherein said transmit timing circuitry is located on a digital integrated circuit.

44. An ultrasonic probe which wirelessly communicates with an ultrasonic diagnostic imaging system for display of ultrasonic information acquired by said probe, comprising:

a multielement transducer array which transmits beams of ultrasonic energy and receives ultrasonic echo signals;

digital transmit timing circuitry coupled to said transducer array to control the transmission of electronically steered and/or focused ultrasound beams by said transducer array; and a wireless transmitter, coupled to said transducer array, which transmits echo signal information, wherein said ultrasound system includes a wireless receiver for receiving said transmitted echo signal information.

45. The ultrasonic probe of claim 44, further comprising a multiplexer coupled between said digital transmit timing circuitry and said multielement transducer array.

46. The ultrasonic probe of claim 44, wherein said digital transmit timing circuitry is located on an integrated circuit.

47. The ultrasonic probe of claim 46, wherein said integrated circuit comprises a beamformer integrated circuit.

48. The ultrasonic probe of claim 47, further comprising a receive beamformer coupled between said multielement transducer array and said wireless transmitter, wherein at least a portion of said receive beamformer is located on said beamformer integrated circuit.

49. The ultrasonic probe of claim 48, further comprising a detector coupled to the output of said receive beamformer, wherein said wireless transmitter transmits detected echo information signals.

50. The ultrasonic probe of claim 44, wherein said wireless transmitter includes a regulator which regulates the transmitted power as a function of either the quality of signals received by said ultrasound system or the distance between said probe and said ultrasound system.

51. An ultrasonic probe which wirelessly communicates with an ultrasonic diagnostic imaging system for display of ultrasonic information acquired by said probe, comprising:

a multielement transducer array which transmits beams of ultrasonic energy and receives ultrasonic echo signals;

transmit timing circuitry coupled to said transducer array to control the transmission of electronically steered and/or focused ultrasound beams by said transducer array; and an r.f. transmitter, coupled to said transducer array, which transmits echo signal information, wherein said ultrasound system includes an r.f. receiver for receiving said transmitted echo signal information.

52. The ultrasonic probe of claim 51, wherein said r.f. transmitter transmits digital echo signal information.

53. The ultrasonic probe of claim 52, wherein said r.f. transmitter transmits compressed digital echo signal information.

54. The ultrasonic probe of claim 51, wherein said r.f. transmitter comprises a spread spectrum transmitter.

55. The ultrasonic probe of claim 51, wherein said r.f. transmitter communicates between said probe and said ultrasound system through simplex operation.

56. The ultrasonic probe of claim 55, wherein said r.f. transmitter receives probe control data originating from the user interface of said ultrasound system.

57. The ultrasonic probe of claim 51, wherein said r.f. transmitter communicates between said probe and said ultrasound system through duplex operation.

58. The ultrasonic probe of claim 57, wherein said r.f. transmitter receives probe control data originating from the user interface of said ultrasound system.

59. An ultrasonic probe which wirelessly communicates with an ultrasonic diagnostic imaging system for display of ultrasonic information acquired by said probe, comprising:

a multielement transducer array which transmits beams of ultrasonic energy and receives ultrasonic echo signals;

transmit timing circuitry coupled to said transducer array to control the transmission of electronically steered and/or focused ultrasound beams by said transducer array; and an omnidirectional transmitter, coupled to said transducer array, which transmits echo signal information, wherein said ultrasound system includes a wireless receiver for receiving said transmitted echo signal information.

60. The ultrasonic probe of claim 59, wherein said omnidirectional transmitter comprises an r.f. transmitter, and wherein said wireless receiver comprises an r.f. receiver.

61. The ultrasonic probe of claim 59, wherein said omnidirectional transmitter transmits digital echo signal information.

62. The ultrasonic probe of claim 61, wherein said omnidirectional transmitter transmits compressed digital echo signal information.

63. The ultrasonic probe of claim 62, wherein said compressed digital echo signal information comprises one of JPEG, MPEG or wavelet compressed data.

64. The ultrasonic probe of claim 59, wherein said omnidirectional transmitter comprises a spread spectrum transmitter.

65. The ultrasonic probe of claim 59, wherein said omnidirectional transmitter communicates between said probe and said ultrasound system through simplex operation.

66. The ultrasonic probe of claim 65, wherein said omnidirectional transmitter receives probe control data originating from the user interface of said ultrasound system.

67. The ultrasonic probe of claim 59, wherein said omnidirectional transmitter communicates between said probe and said ultrasound system through duplex operation.

68. The ultrasonic probe of claim 67, wherein said omnidirectional transmitter receives probe control data originating from the user interface of said ultrasound system.

69. The ultrasonic probe of claim 59, wherein said ultrasound system further includes a probe control for controlling ultrasonic scanning by an ultrasonic probe, and wherein said probe further comprises:

an omnidirectional receiver which receives scanning control signals from said ultrasound system in response to operation of said probe control for operation of said transmit timing circuitry.

70. The ultrasonic probe of claim 59, wherein said transmit timing circuitry controls the transmission of ultrasound beams for B mode or Doppler imaging.

71. The ultrasonic probe of claim 59, wherein said omnidirectional transmitter has a transmitter bandwidth of at least 4 MBPS.

72. The ultrasonic probe of claim 71, wherein said omnidirectional transmitter has a transmitter bandwith of at least 11 MBPS.

73. The ultrasonic probe of claim 59, wherein said omnidirectional transmitter includes a superhetrodyne modulator.

74. The ultrasonic probe of claim 59, further comprising a receive beamformer coupled between said transducer array and said omnidirectional transmitter.

75. The ultrasonic probe of claim 74, further comprising a detector coupled between said received beamformer and said omnidirectional transmitter, wherein said omnidirectional transmitter transmits detected echo signal information to said ultrasound system.

76. The ultrasonic probe of claim 59 or 75, wherein said omnidirectional transmitter transmits echo signal information in packets of data.

77. The ultrasonic probe of claim 59, wherein said omnidirectional transmitter includes a regulator which regulates the transmitted power as a function of either the quality of signals received by said ultrasound system or the distance between said probe and said ultrasound system.

\* \* \* \* \*